United States Patent [19]

Ando et al.

[11] Patent Number: 4,768,378

[45] Date of Patent: Sep. 6, 1988

[54] HUMIDITY DETECTING CIRCUIT

[75] Inventors: Yuzi Ando, Nara; Yuichi Mori, Yamatokoriyama; Hirokazu Tahara, Osaka; Tatsuya Tsuda, Osaka; Masato Nakatani, Osaka; Masanobu Fujii, Yao, all of Japan

[73] Assignee: Sharp Kabushiki Kaisha, Osaka, Japan

[21] Appl. No.: 10,794

[22] Filed: Feb. 4, 1987

[30] Foreign Application Priority Data

Feb. 4, 1986 [JP] Japan .................................. 61-23556
Feb. 6, 1986 [JP] Japan .................................. 61-15991

[51] Int. Cl.$^4$ .......................................... G01W 1/00
[52] U.S. Cl. ..................................... 73/336.5; 73/29
[58] Field of Search ....................... 73/29, 336.5, 27 R

[56] References Cited

U.S. PATENT DOCUMENTS 4,419,888 12/1983 Kitamura et al. .................. 73/336.5

Primary Examiner—Stewart J. Levy
Assistant Examiner—Joseph W. Roskos
Attorney, Agent, or Firm—Birch, Stewart, Kolasch & Birch

[57] ABSTRACT

A humidity detecting circuit for detecting the ambient humidity in a cooking chamber, which includes a constant current source, a first temperature-detecting resistor self-heated by the constant current source to detect the ambient humidity and having one terminal connected to an output terminal of the constant current source, and a second temperature-detecting resistor having one terminal connected to the one terminal of the first temperature-detecting resistor to detect the ambient temperature. An operational amplifier having an inverting input terminal, a noninverting input terminal and an output terminal is provided, the inverting input terminal being connected to the other terminal of the second temperature-detecting resistor so that the terminal voltage of the first temperature-detecting resistor may be inputted into the inverting input terminal through the second temperature-detecting resistor. A feedback resistor is associated with the operational amplifier and has one terminal connected to the output terminal of the operational amplifier and an other terminal connected to the inverting input terminal of the operational amplifier.

7 Claims, 8 Drawing Sheets

HUMIDITY DETECTING CIRCUIT

BACKGROUND OF THE INVENTION

The present invention generally relates to an electronic detection circuit and more particularly, to a humidity detecting circuit for detecting completion of cooking through the humidity level in a cooker such as a microwave oven or the like.

Such a humidity detecting circuit is incorporated in a humidity detecting device employed in the microwave oven or the like.

Figure 1:
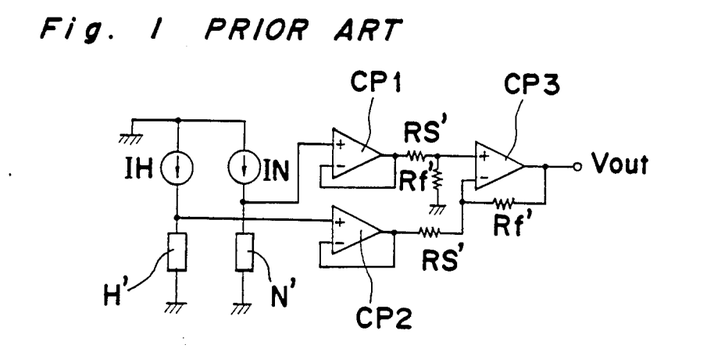
FIG. 1 is an electronic circuit diagram of the conventional humidity detecting circuit for detecting the completion of cooking within a microwave oven (already referred to)

The conventional humidity detecting circuit is constructed as shown, for example, in FIG. 1. More specifically, with employment of a first temperature-detecting resistor H' and a second temperature-detecting resistor N', the first temperature-detecting resistor H' exhibits an output voltage VH, through self-heating by a large and constant current source IH. Both of the temperature-detecting resistors H' and N' have linear resistance values with positive temperature coefficients by the use of metallic films., the second temperature-detecting resistor N' exhibits a voltage VN proportional to the ambient temperature by a very small and constant current source IN. When a constant current value is set so that a voltage difference between the two temperature-detecting resistors H' and N' i.e., the value of VN−VH, becomes zero in the dry condition, a difference voltage also becomes zero independent of the ambient temperature. When air contains steam through progress of cooking in the microwave oven, the first temperature-detecting resistor H', self-heated to 150° C. through 200° C., is deprived of heat by the steam, thereby lowering the temperature thereof, and resulting in the voltage across the first temperature-detecting resistor H' being lowered. As the output voltage VN on the side of the second temperature-detecting resistor N' does not change, VN—VH is not zero as a result. This voltage is amplified by a factor of Rf/RS' by an operational amplifier CP3 to detect the existence of humidity. An operational amplifier CP1 and an operational amplifier CP2 are voltage followers for transmitting the output voltages VN and VH to the operational amplifier CP3.

The following equation is established, where resistance values at 0° C. of the first and the second temperature-detecting resistors H' and N' are respectively RH and RN, temperature coefficients thereof are respectively $\alpha H$ and $\alpha N$, and the resistance values thereof at the temperatures tH and tN are respectively rH and rN:

$$rH = RH(1 + \alpha H \cdot tH) \quad (1)$$

$$rN = RN(1 + \alpha N \cdot tN) \quad (2)$$

Meanwhile, a temperature rise (tH−tN) through self-heating is linearly related to the amount of power consumed by the first temperature-detecting resistor H'.

As tN is equal to the ambient temperature, $$rH \cdot IH^2 = hm(tH - tN)S \quad (3).$$

Hereupon, hm is the heat transfer coefficient and S is a surface area of the first temperature-detecting resistor H'. From the equations of (1) and (3), the following equation can be obtained.

$$rH = \frac{RH}{1 - \frac{\alpha H \cdot IH^2}{hm \cdot S} RH} (1 + \alpha H \cdot tN) \quad (4)$$

As the antecedent of the equation of (4) becomes a constant when hm is constant in the dry condition, the first temperature-detecting self-heating resistor H' has the following resistance value at 0° C.

$$\frac{RH}{1 - \frac{\alpha H \cdot IH^2}{hm \cdot S} RH}$$

Accordingly, the first temperature detecting-resistor H' in this case is equivalent to a temperature-detecting resistor having the temperature coefficient of $\alpha H$.

The output voltages of the operational amplifiers CP1 and CP2 in FIG. 1 are respectively as follows.

$$VH = rH \cdot IH = \frac{RH \cdot IH}{1 - \frac{\alpha H \cdot IH^2}{hm \cdot S} RH} = (1 + \alpha H \cdot tN) \quad (5)$$

$$VN = rN \cdot IN = RN \cdot IN(1 + \alpha N \cdot tN) \quad (6)$$

An output Vout of the operational amplifier CP3 is as follows.

$$Vout = \frac{Rf}{RS'} (VN - VH) \quad (7)$$

$$= \frac{Rf}{RS'} \left\{ RN \cdot IN(1 + \alpha N \cdot tN) - \frac{RH \cdot IH}{1 - \frac{\alpha H \cdot IH^2 \cdot RH}{hm \cdot S}} (1 + \alpha H \cdot tN) \right\}$$

When IN and IH are set so that $$\alpha H = \alpha N, \text{ and } RN \cdot IN = \frac{RH \cdot IH}{1 - \frac{\alpha H \cdot IH^2 \cdot RH}{hm \cdot S}}$$

may be established to set as a constant, Vout of the equation (7) normally becomes zero as hm is constant under the dry condition. The following equation can be obtained from rewritting the equation (7), $$Vout = \frac{Rf}{RS'} \left( RN \cdot IN - \frac{RH \cdot IH}{1 - \frac{\alpha H \cdot IH^2 \cdot RH}{hm \cdot S}} \right) (1 + \alpha N \cdot tN) \quad (7)'$$

Figure 2:
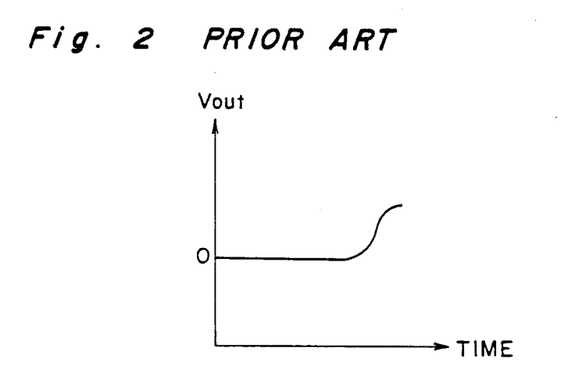
FIG. 2 is a graphical diagram showing the characteristics with respect to time of an output voltage produced from the conventional humidity detecting circuit of FIG. 1 (already referred to)

Although hm is constant in the dry condition, hm increases as the steam starts to come out of the cooked food in course of the cooking operation. At this moment, Vout increases rapidly from zero so that humidity detection may be performed. A change of Vout with time is shown in FIG. 2.

In the conventional humidity detecting circuit of FIG. 1, however, it is required to provide a large number of circuit elements such as two constant-current sources IH and IN, three of the operational amplifiers CP1, CP2 and CP3, and the like. Furthermore, it is very difficult to incorporate IH and IN of the two constant-current sources into the circuit so as to meet the conditions the equation of (7).

SUMMARY OF THE INVENTION

Accordingly, the present invention has been developed with a view to substantially eliminating the above described disadvantages inherent in the prior art humidity detecting circuit, and has for its essential object to provide an improved humidity detecting circuit which is not required to jointly incorporate two constant-current sources thereinto.

Another important object of the present invention is to provide a humidity detecting circuit of the above described type which is simple in construction and stable in functioning, and can be readily manufactured at low cost.

In accomplishing these and other objects, according to one preferred embodiment of the present invention, there is provided a humidity detecting circuit for detecting ambient humidity, which includes a constant current source, a first temperature-detecting resistor self-heated by the constant current source to detect ambient humidity and having one terminal connected to an output terminal of the constant current source, a second temperature-detecting resistor having one terminal connected to said one terminal of the first temperature-detecting resistor to detect the ambient temperature, an operational amplifier having an inverting input terminal, a noninverting input terminal and an output terminal, said inverting input terminal being connected to the other terminal of the second temperature-detecting resistor so that the terminal voltage of the first temperature-detecting resistor may be inputted into the inverting input terminal through the second temperature-detecting resistor, and a feedback resistor associated with the operational amplifier and having one terminal connected to the output terminal of the operational amplifier and the other terminal connected to the inverting input terminal thereof.

BRIEF DESCRIPTION OF THE DRAWINGS

These and other objects and features of the present invention will become apparent from the following description taken in conjunction with the preferred embodiment thereof with reference to the accompanying drawings, throughout which like parts are designated by like reference numerals, and in which.

DETAILED DESCRIPTION OF THE PREFERRED EMBODIMENT

The principle of a humidity detecting circuit for detecting the end of cooking in a microwave oven through the level of humidity in accordance with the present invention will be described hereinafter with reference to FIGS. 3 and 4.

Figure 3:
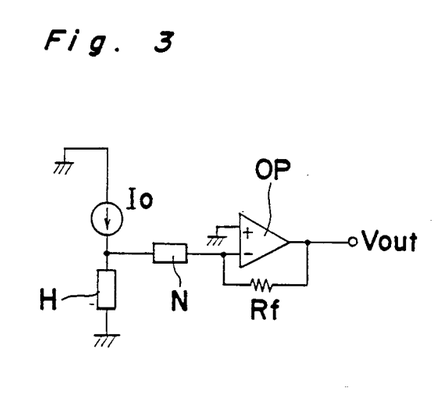
FIG. 3 is a fundamental electronic circuit diagram of a humidity detecting circuit according to the present invention for detecting the completion of cooking within the microwave oven.
Figure 4:
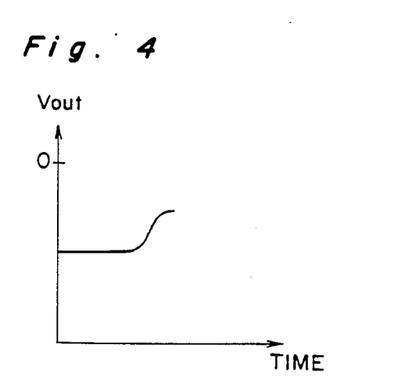
FIG. 4 is a graphical diagram showing the characteristics with respect to time of the output voltage produced from the humidity detecting circuit of FIG. 3.

Although an electronic circuit according to the present invention as shown in FIG. 3 is substantially the same as the conventional electronic circuit as shown in FIG. 1 to the extent that a first temperature-detecting resistor H is self-heated by a constant-current source Io, the former is different from the latter in that a second temperature-detecting resistor N is interposed between an output from the first temperature-detecting resistor H and an inverting input into an operational amplifier OP.

Namely, the electronic circuit according to the present invention includes a first temperature-detecting resistor H which performs a self-heating operation for detecting the humidity, a second temperature-detecting resistor N for detecting the ambient temperature, a constant-current source Io, an operational amplifier OP and a feedback resistor Rf associated with the operational amplifier OP. More specifically, one terminal of the first temperature-detecting resistor H is directly connected to the output terminal of the constant-current source Io so that the first temperature-detecting resistor H is self-heated by the constant-current source Io, while the other terminals of the resistor H and the current source Io are grounded. The terminal voltage of the first temperature-detecting resistor H is applied to the inverting input terminal (i.e., (−) terminal) of the operational amplifier OP through a second temperature-detecting resistor N. The output from the operational amplifier OP is negatively fed back to the inverting input terminal thereof through a feedback resistor Rf, with a noninverting input terminal (i.e., (+) terminal) thereof being grounded. Accordingly, components provided in the humidity detecting circuit of the present invention are extremely reduced in number as compared with the conventional humidity detecting circuit.

On the assumption that rH<<rN in FIG. 3, the terminal voltage VH of the first temperature-detecting resistor H is as follows in the equation (5).

$$VH = \frac{RH \cdot Io^2}{1 - \frac{\alpha H \cdot Io^2 \cdot RH}{hm \cdot S}} (1 + \alpha H \cdot tN) \quad (8)$$

As the gain of the operational amplifier OP is $$\frac{Rf}{rH + rN} \approx \frac{Rf}{rN}$$

ps under the condition of rH<<rN, the output Vout can be obtained as follows for the selection of αH=αN.

$$Vout = \frac{Rf}{-rN} \cdot VH \quad (9)$$

$$= \frac{RH \cdot Io \cdot Rf}{-\left(1 - \frac{\alpha H \cdot Io^2 \cdot RH}{hm \cdot S}\right) \cdot RN}$$

Since the heat transfer coefficient hm is constant in the dry condition, the output Vout becomes a negative constant value. As the hm increases because of steam produced in the course of cooking, the absolute value of Vout becomes small so that a time lapse of the output as shown in FIG. 4 may be obtained.

Figure 5:
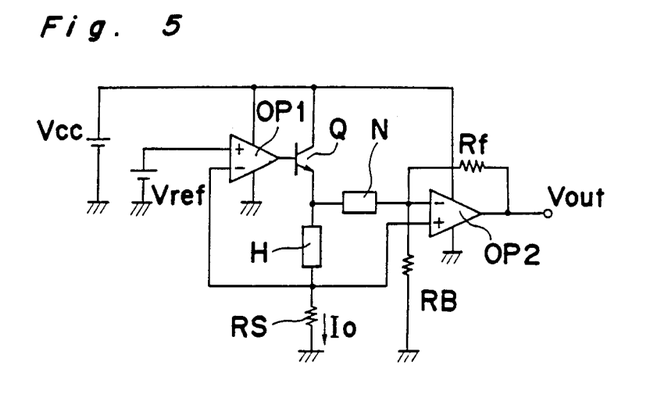
FIG. 5 is an electronic circuit diagram showing a preferred embodiment of the humidity detecting circuit of FIG. 3.

FIG. 5 shows one preferred embodiment of the present invention. Although both positive and negative power sources are required for the operational amplifier OP in the electronic circuit as shown in FIG. 3, the electronic circuit shown in FIG. 5 is simplified so that only a positive power source is required.

In FIG. 5, the constant-current circuit is composed of a first operational amplifier OP1, a transistor Q, a resistor RS and a reference power source Vref to feed the constant current Io=Vref/RS to the first temperature-detecting resistor H. More specifically, the output voltage from the reference power source Vref is applied to the noninverting input terminal of the first operational amplifier OP1, and one terminal of the first temperature-detecting resistor H is directly connected to the emitter of the transistor Q which amplifies the output current from the first operational amplifier OP1, with the output from the first operational amplifier OP1 being applied to the base of the transistor Q. The other terminal of the first temperature-detecting resistor H is grounded through the resistor RS and is also connected to the inverting input terminal (i.e., (−) terminal) of the first operational amplifier OP1 so that upon amplification of the output from the first operational amplifier OP1, it is negatively fed back to the inverting input terminal through the first temperature-detecting resistor H. Furthermore, the terminal voltage of the first temperature-detecting resistor H is applied to the inverting input terminal of a second operational amplifier OP2 through a second temperature-detecting resistor N for detecting the ambient temperature as in FIG. 3. The terminal voltage of the resistor RS is directly applied to the noninverting input terminal of the second operational amplifier OP2. The output from the second operational amplifier OP2 is negatively fed back to the inverting input terminal thereof through a feedback resistor Rf. A junction between the second temperature-detecting resistor N and the inverting input terminal of the second operational amplifier OP2 is grounded through a resistor RB. In addition, another power source Vcc is provided in this electronic circuit so that the output voltage from the power source Vcc is applied to the first operational amplifier OP1, to the second operational amplifier OP2 and to the collector of the transistor Q.

The output voltage Vout from the operational amplifier OP2 in FIG. 5 is derived as follows in case of αH=αN.

$$Vout = -\frac{RH}{RN\left(1 - \frac{\alpha H \cdot RH \cdot Vref^2}{hm \cdot S \cdot RS^2}\right)} \times \frac{Rf}{RS}. \quad (10)$$

$$V_{ref} + \left(1 + \frac{Rf}{RB}\right) V_{ref}$$

Figure 6:
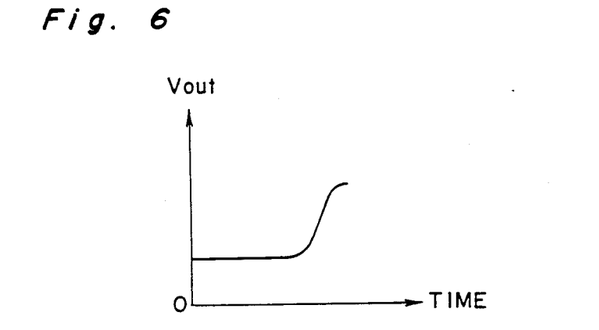
FIG. 6 is a graphical diagram showing the characteristics with respect to time of the output voltage produced from the electronic circuit of FIG. 5.

First, the resistor RB which is connected to the negative input terminal of the second operational amplifier OP2 is kept adjusted so that Vout may become a constant value in the initial condition of cooking. When hm increases by the steam of the cooked food produced in the course of the cooking operation, the first term in the equation of (10) decreases. As a result, Vout rapidly increases with time as shown in FIG. 6.

In the principle shown in FIG. 3, although selection is required to have $\alpha H = \alpha N$, such selection is hard to be achieved in terms of performance of the temperature detection resistance.

In the other embodiment of the humidity detecting circuit of the present invention, therefore, the detection of the humidity is adapted to be performed even if the relation of $\alpha H = \alpha N$ is not established.

The other embodiment of the humidity detecting circuit according to the present invention will be described hereinafter with reference to FIG. 7.

What is different from the above described electronic circuit shown in FIG. 3 is that the terminal voltage VH of the first temperature-detecting resistor H is applied to the inverting input terminal of the operational amplifier OP through the second temperature-detecting resistor N and a resistor Rc additionally connected in series therewith.

More specifically, there are provided a first temperature-detecting resistor H which performs the self-heating operation for detection of the humidity, a second temperature-detecting resistor N for detecting the ambient temperature, a constant-current source Io, an operational amplifier OP, a feedback resistor Rf associated with the operational amplifier OP and a resistor Rc connected in series with the second temperature-detecting resistor N. The first temperature-detecting resistor H is self-heated by the constant-current source Io, and the terminal voltage of the first temperature-detecting resistor H is inputted into the inverting input terminal of the operational amplifier OP through the second temperature-detecting resistor N and the resistor Rc.

The humidity detecting circuit may be constructed without making $\alpha H$ equal to $\alpha N$ in this circuit.

Figure 7:
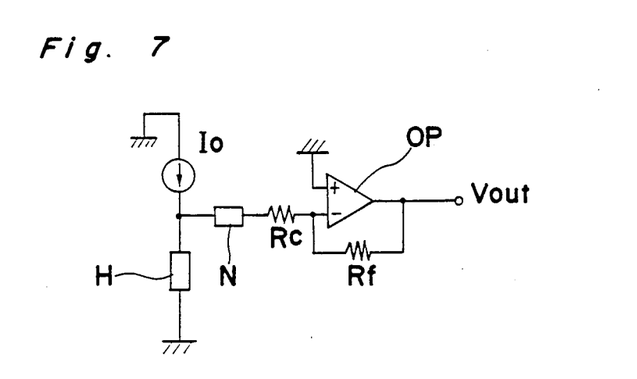
FIG. 7 is a fundamental electronic circuit diagram of the humidity detecting circuit according to another embodiment of the present invention for detecting cooking completion within a microwave oven.

The gain of the operational amplifier shown in FIG. 7 is as follows.

$$\frac{Rf}{rH + rN + Rc} \approx \frac{RF}{rN + Rc} \quad (11)$$

Accordingly, the output Vout is derived as follows.

$$V_{out} = \frac{Rf}{-(rN + Rc)} \cdot VH \quad (12)$$

$$= \frac{Rf \cdot Io}{-\left(1 - \frac{\alpha H \cdot Io^2 \cdot RH}{hm \cdot S}\right)} \times$$

$$\frac{RH(1 + \alpha H \cdot tN)}{RN(1 + \alpha N \cdot tN) + Rc}$$

Hereupon, when Rc is selected so that the following equation may be established $$\frac{RH(1 + \alpha H \cdot tN)}{RN(1 + \alpha N \cdot tN) + Rc} = \text{constant}, \quad (13)$$

the output Vout is derived as follows.

$$V_{out} = \frac{Rf \cdot Io}{-\left(1 - \frac{\alpha H \cdot Io^2 \cdot RH}{hm \cdot S}\right)} \times C$$

In this equation, C is as a constant.

Since hm is constant in the dry condition, the output Vout is a constant value. As hm is increased by the steam produced in the course of the cooking operation, the absolute value of Vout becomes smaller so that such time lapse outputted as shown in FIG. 6 may be provided.

As the humidity detecting circuit of the present invention is constructed as described hereinabove, the completion of the cooking in the microwave oven or the like can be detected by the humidity level through the adjusting operation of the resistors connected in series without requiring the respective humidity coefficients $\alpha H$ and $\alpha N$ to be equal to each other, thus resulting in a remarkable effect in the automatic heating of food.

Various examples in construction of a humidity sensor incorporated in a humidity detecting device, to which the present invention is applied, will be explained hereinafter.

Figure 8:
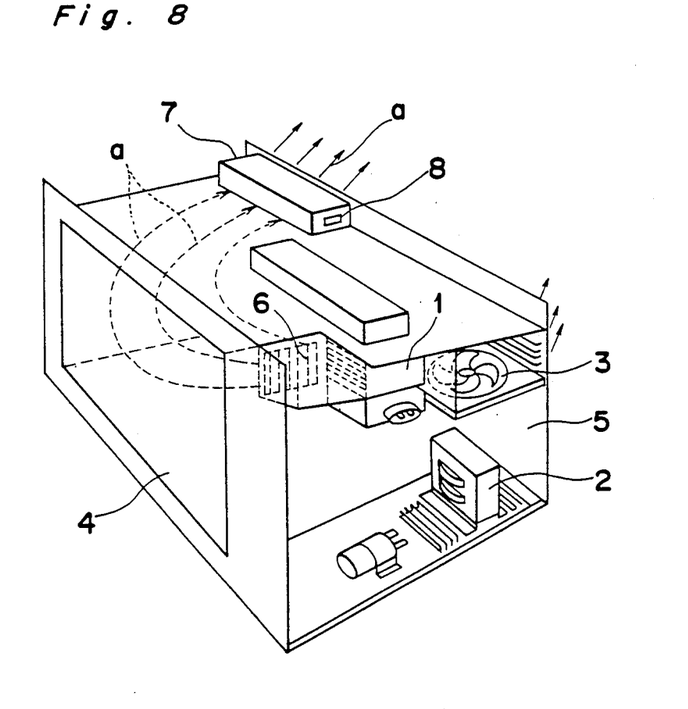
FIG. 8 is a perspective view of a microwave oven to which the present invention is applied.
Figure 9:
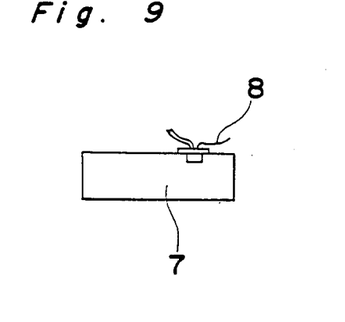
FIG. 9 is a side elevational view of an exhaust duct having thereon a humidity sensor incorporated in a humidity detecting device.

FIG. 8 shows a microwave oven having a humidity detecting device incorporating therein the humidity detecting circuit of the present invention. The microwave oven shown in FIG. 8 is provided with a magnetron 1, a high-tension transformer 2, a cooling fan 3 for cooling the magnetron 1 and the high-tension transformer 2, a heating chamber 4 and an exhaust duct 7, with the magnetron 1, the high-tension transformer 2 and the cooling fan 3 being accommodated within a main body 5 outside the heating chamber 4. The radiation from the magnetron 1 itself is discharged to the exhaust duct 7 together with warm air (a) which is produced by an object to be heated, within the heating chamber 4 from a ventilation opening 6 defined in a chamber wall of the heating chamber 4. A humidity sensor 8 is arranged, as shown in FIG. 9, in the exhaust duct 7.

Figure 10:
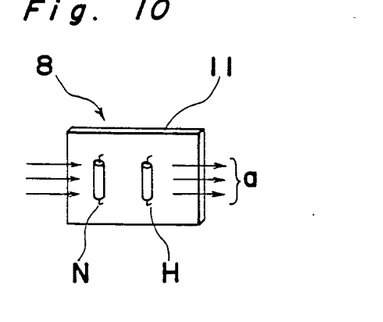
FIG. 10 is a perspective view of the humidity sensor of FIG. 9, which particularly shows a first example thereof.

FIG. 10 is a first example of the humidity sensor 8 for detecting the humidity in the atmosphere within the exhaust duct 7, which sensor 8 is provided with the first temperature-detecting resistor H to be self-heated or to be heated by a heat source, the second temperature-detecting resistor N juxtaposed with the first temperature-detecting resistor H and for detecting the humidity within the atmosphere, and a base plate 11 for supporting thereon the first and the second temperature-detecting resistors H and N.

Preferably, the humidity sensor 8 is further provided with a rectifier box as shown in the examples described hereinbelow.

Figure 13:
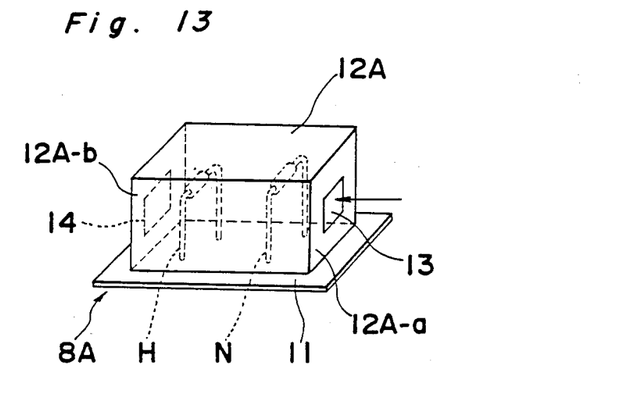
FIG. 13 is a perspective view of the humidity sensor, which particularly shows a second example thereof.

FIG. 13 shows a second example of the humidity sensor 8A which is provided with a rectifier box 12A in the form of a rectangular parallelpiped having an opened bottom and surrounding the first and the second temperature-detecting resistors H and N. The rectifier box 12A includes a front plate 12A—a having a rectangular inlet opening 13 and a rear plate 12A—b having a rectangular outlet opening 14, wherein the amount of air introduced into the rectifier box 12A is controlled by both the inlet and the outlet openings 13 and 14, with the rectifier box 12A being arranged so that the front and the rear plates 12A—a and 12A—b are perpendicular to the flowing direction of the ventilation air within the ventilation passage.

Figure 11:
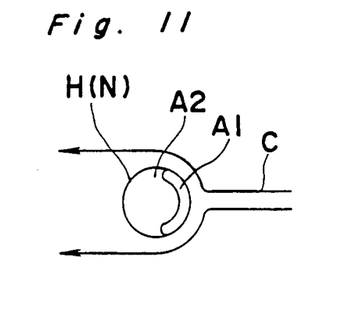
FIG. 11 is a side elevational view of one temperature-detecting resistor on an enlarged scale, showing an uneven temperature produced thereon in a case where no rectifier box is provided.
Figure 12:
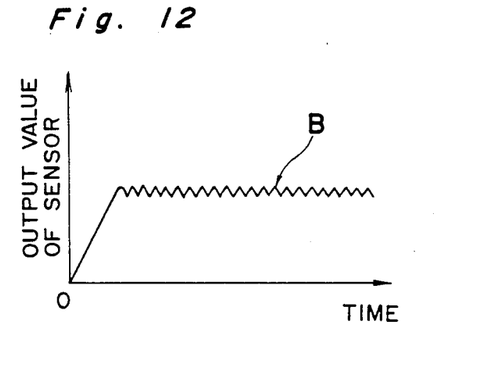
FIG. 12 is a graphical diagram showing an output voltage from the humidity sensor of FIG. 10 in a case where no rectifier box is provided.
Figure 14:
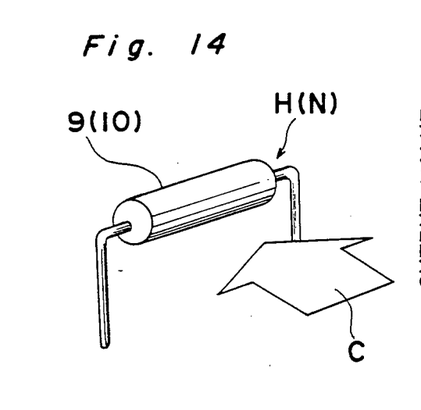
FIG. 14 is a perspective view of one of the temperature-detecting resistors mounted in the humidity sensor of FIG. 13, on an enlarged scale, showing a state in which exhaust air is brought into contact with the temperature-detecting resistor.

By the above described construction, the air C which enters the rectifier box 12A through the exhaust duct 7 flows against the first and the second temperature-detecting resistors H and N. In an atmosphere of 20° C., for example, when the exhaust air containing steam of 50° C. is caused to flow against temperature detecting portions 9 and 10 of the temperature-detecting resistors H and N as shown in FIG. 14 under the condition that no rectifier box is provided, the strong or weak contact of the exhaust air against the surfaces of the temperature-detecting resistors H and N may take place as shown in FIG. 11 to cause uneven temperatures A1 and A2, because the flow speed of the exhaust air C is so high that a rectifying operation is not performed. Accordingly, an unevenness undesirably arises even in the response speed with respect to the temperature of the exhaust air, thus resulting in major oscillation with respect to output values of the temperature-detecting resistors H and N as shown in FIG. 12.

Figure 15:
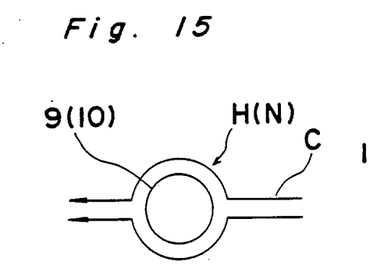
FIG. 15 is a side elevational view of FIG. 14 similar to FIG. 11, showing the flow of exhaust air.

However, when the exhaust air is introduced into the rectifier box 12A to reduce the flow speed thereof and to perform the rectifying operation, the contacting of the exhaust air becomes uniform so that the exhaust air flows along the whole surface of the temperature-detecting resistors H and N as shown in FIG. 15, thus resulting in uniform temperature on the surfaces of the temperature-detecting resistors H and N.

Figure 16:
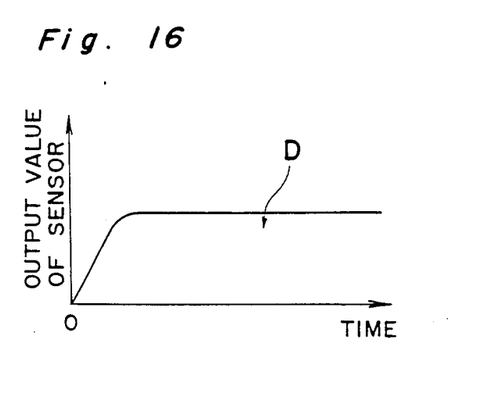
FIG. 16 is a graphical diagram silimar to that in FIG. 12, which particularly shows the output voltage from humidity sensor of FIG. 13.

As a result, the output signal D is stabilized as shown in FIG. 16. Accordingly, the stabilized output signal obtained allows that the correct heating time to be calculated.

Figure 17:
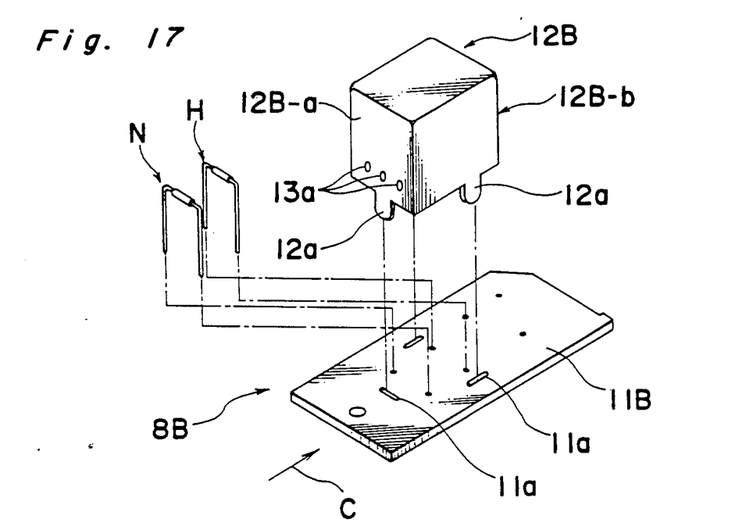
FIG. 17 is an exploded perspective view of the humidity sensor, which particularly shows a third example thereof.

FIG. 17 shows a third example of the humidity sensor 8B. When the inlet opening 13 of the rectifier box 12A is small in FIG. 13, the opening 13 may be stopped up by foreign substances such as oil, food particles or the like contained in the steam produced in the course of cooking. In this case, the air containing the steam never flows against the first and the second temperature-detecting resistors H and N so that the humidity cannot be detected.

In this example, therefore, the rectifier box 12B is provided with the front plate 12B-a having a plurality of inlet openings 13a defined therein. The rectifier box 12B is securely mounted on the base plate 11B in a manner that leg portions 12a of the rectifier box 12B are initially extended through respective holes 11a defined in the base plate 11B and are bent thereafter. The other construction is similar to that in the second example.

Suppose that one inlet opening 13a is stopped up by foreign substances in such construction as described hereinabove, the air C is still permitted to flow into the rectifier box 12B through the other inlet openings 13a to make it possible to perform a stable humidity-detection.

Figure 18:
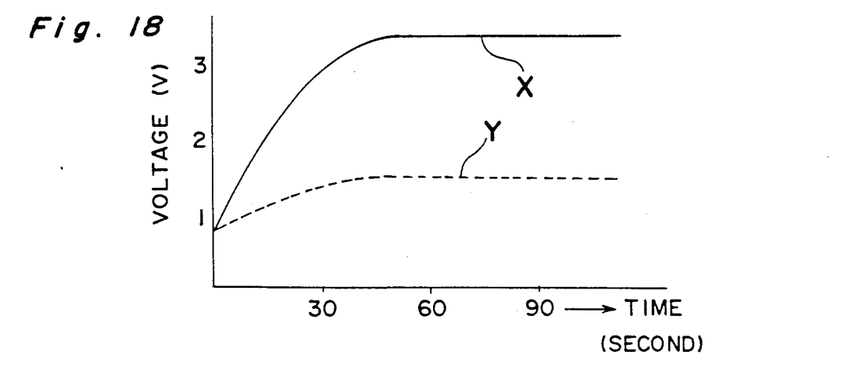
FIG. 18 is a graphical diagram showing the output voltages from the humidity detecting circuit of FIG. 5 in a case where no rectifier box is provided and in a case where the rectifier box is provided, with a cooling fan provided in the microwave oven having been operated.

It is to be noted that the output fluctuation can be reduced in the second and the third examples, because the air speed is lowered even when the voltage to be supplied has been changed. More specifically, in the case where the humidity detecting circuit shown in FIG. 5 is employed, the output voltages Vout are graphically shown in FIG. 18 with respect to the humidity sensor 8 described in the first example thereof and to the humidity sensor 8A or 8B described in the second or the third example thereof, when the cooling fan 3 has been operated from the stop condition. In FIG. 18, the output voltage Vout produced from the humidity sensor 8 in the first example is shown by X and the output voltage Vout produced from the humidity sensor 8A or 8B in the second or the third examples is shown by Y. In the latter, the voltage change is reduced, since the speed of the air flowing against the temperature-detecting resistors H and N is lowered.

Figure 19:
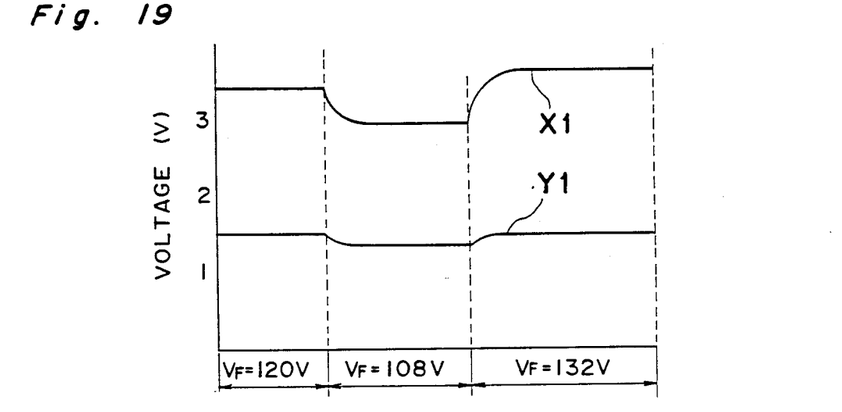
FIG. 19 is a graphical diagram showing the characteristics of the output voltages from the humidity detecting circuit of FIG. 5, in a case where the service voltage of the cooling fan has been varied while the output voltage is kept constant.

Furthermore, FIG. 19 graphically shows the characteristics in the case where the voltage supplied to the cooling fan 3 is changed when the output voltage Vout becomes constant upon rotation of the cooling fan 3. In FIG. 19, X1 shows the case in the first example and Y1 shows the case in the second or the third example. In the latter, the output fluctuation is controlled to be extremely small.

Figure 20:
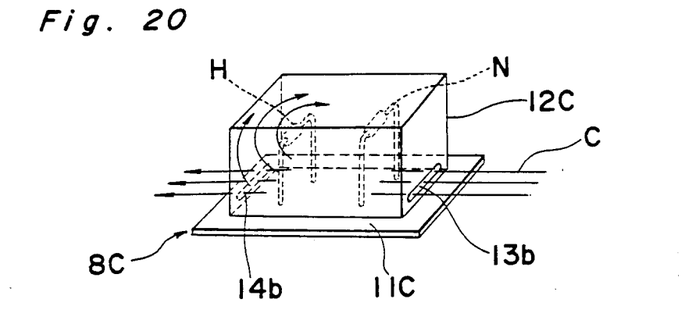
FIG. 20 is a view similar to FIG. 13, which particularly shows a fourth example of the humidity sensor.
Figure 21:
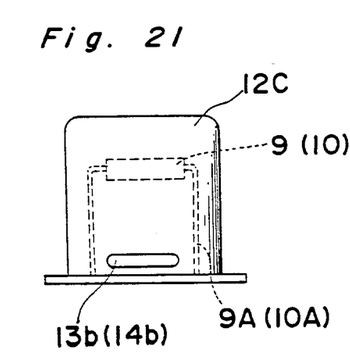
FIG. 21 is a front elevational view of the humidity sensor of FIG. 20.

FIGS. 20 and 21 show a fourth example of the humidity sensor 8C, wherein the inlet opening 13b and the outlet opening 14b each elongated horizontally are formed at the lower portion of the rectifier box 12C, with the horizontal width of each elongated opening 13b or 14b being caused to be shorter than a distance between a pair of spaced lead leg portions 9A or 10A of the respective temperature-detecting resistors H or N so that the air C introduced into the rectifier box 12C may not be brought into direct contact against the first and the second temperature-detecting resistors H and N. As a result, the hot air is lowered in its flow speed to perform the rectifying operation and is caused to substantially uniformly contact against the whole surface of the temperature-detecting resistors H and N to rectify the temperature variation which tends to occur thereon. The other construction of the humidity sensor 8C in this example is similar to that in the above described second example.

In the above described construction, the air C which is introduced into the rectifier box 12C has a turbulent flow to flow along the whole surface of the temperature-detecting resistors H and N as shown in FIG. 15 so that the contacting of the exhaust air C becomes uniform.

Figure 22:
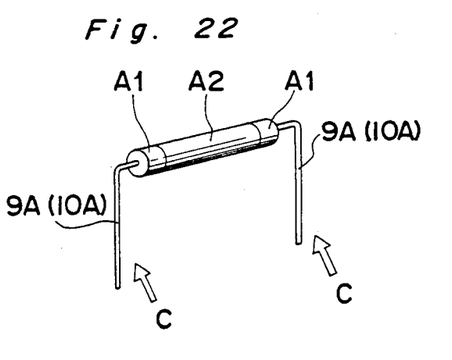
FIG. 22 is a perspective view of the temperature-detecting resistor on an enlarged scale, similar to FIG. 14, showing the uneven temperature of a temperature detecting porton thereof in a case where the exhaust air is brought into contact with lead leg portions thereof.

It is to be noted here that if the horizontal width of each opening 13b or 14b is caused to be longer than the distance between the pair of lead leg portions 9A or 10A of respective temperature-detecting resistors H or N, the exhaust air passing through the inlet opening 13b directly collides against the leg portions 9A and 10A of the temperature-detecting resistors H and N as shown in FIG. 22 so that thermal conduction is caused from the leg portions 9A and 10A to raise the temperature initially from both end portions A1 of the temperature detecting portions 9 and 10, thus resulting in undesirable temperature differences between both end portions A1 and the central portion A2 thereof. Accordingly, the unevenness takes place even at the response speed with respect to the temperature of the exhaust air so that such oscillation as shown in FIG. 12 appears in the output Vout produced from these elements 9 and 10.

In this example, however, since the horizontal width of each openings 13b or 14b is caused to be shorter than the distance between the pair of leg portions 9A or 10A, the exhaust air which has entered the rectifier box 12C turns the turbulent flow to flow along the entire surfaces of the temperature-detecting resistors H and N, and the collision of the exhaust air thereagainst becomes uniform to settle the uneven temperature on the surfaces of the temperature detecting portions 9 and 10 or the uneven response speed with respect thereto. As a result, the output signal D˙ is desirably stabilized as shown in FIG. 16.

Figure 23:
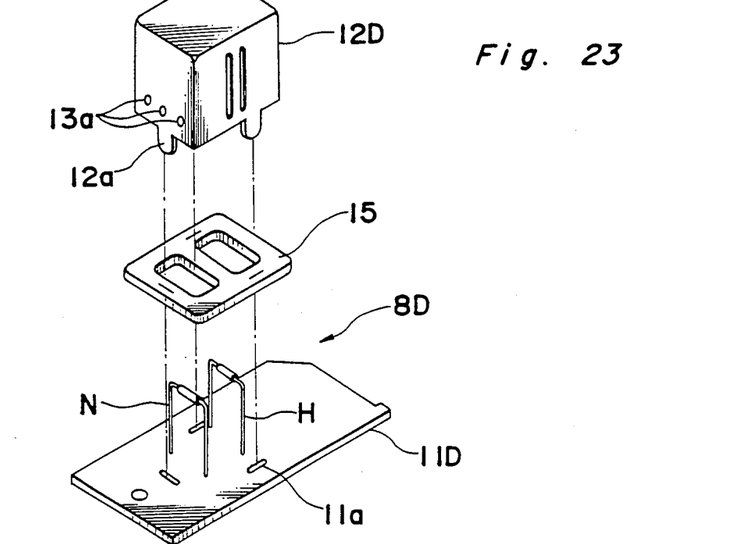
FIG. 23 is a view similar to FIG. 17, which particularly shows a fifth example of the humidity sensor.
Figure 24:
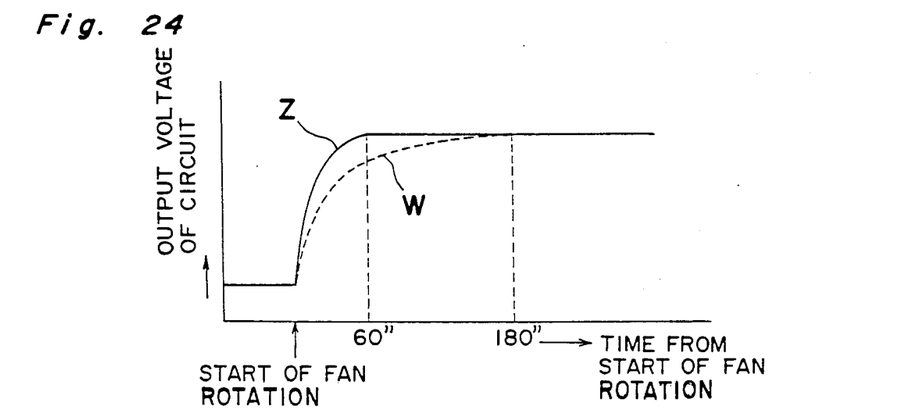
FIG. 24 is a graphical diagram showing the characteristics with respect to time of the output voltages from the humidity detecting circuit of FIG. 5, in cases where two kinds of different materials are applied to the rectifier box, with the cooling fan having been operated.

A fifth example of the humidity sensor 8D is illustrated in FIGS. 23 and 24, wherein the rectifier box 12D is made of metal such as aluminum or the like having a superior heat conductivity. It is to be noted in this example that a heat insulating packing 15 is provided to prevent the base plate 11D from being subjected to thermal influence. The other elements of the humidity sensor 8D in this example is similar to that of the aforegoing third example.

FIG. 24 shows the characteristics with respect to time required from the initial rotation of the cooling fan 3 to the stabilization of the circuit output in a case where the rectifier box 12D is made of polypropylene resin having a thickness of 1 mm and in a case where it is made of aluminum having a thickness of 0.6 mm. As clearly shown in FIG. 24, although the circuit requires approximately three minutes to be stabilized in output therefrom in the case of the polypropylene resin as shown by W, it advantageously requires only approximately fifty seconds to be stabilized in the case of a metal such as aluminum or the like having superior thermal conductivity.

Figure 25:
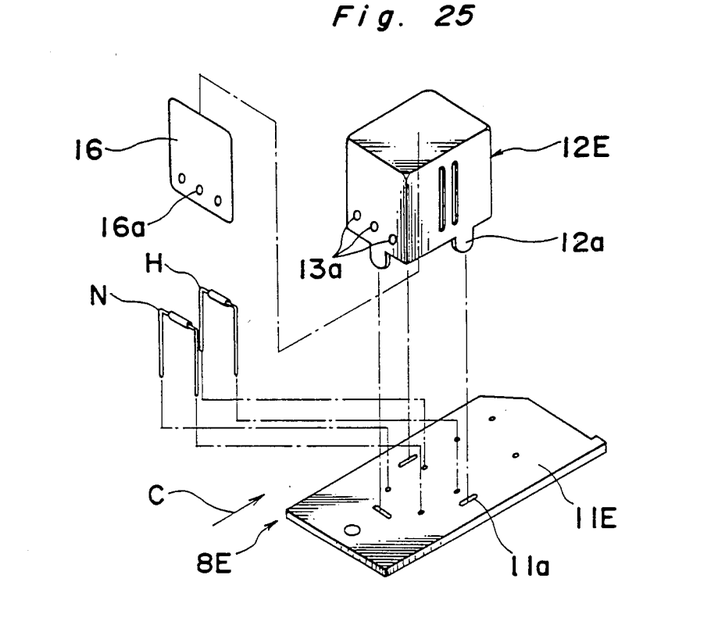
FIG. 25 is a view similar to FIG. 17, which particularly shows a sixth example of the humidity sensor.

A sixth example of the humidity sensor 8E is illustrated in FIG. 25, wherein a partition plate 16 is provided between the first temperature-detecting resistor H and the second temperature-detecting resistor N in the rectifier box 12E to partition the two resistors H and N from each other, with one or more openings 16a being formed in the partition plate 16 to enable the exhaust air to pass therethrough. The other construction of the humidity sensor 8E in this example is similar to that in the aforementioned third example.

By the above described construction, the air C introduced into the rectifier box 12E can be reduced in its speed variation so that the variation in hm of the equation (9) caused thereby can be minimized to provide the correct humidity detection.

Figure 26:
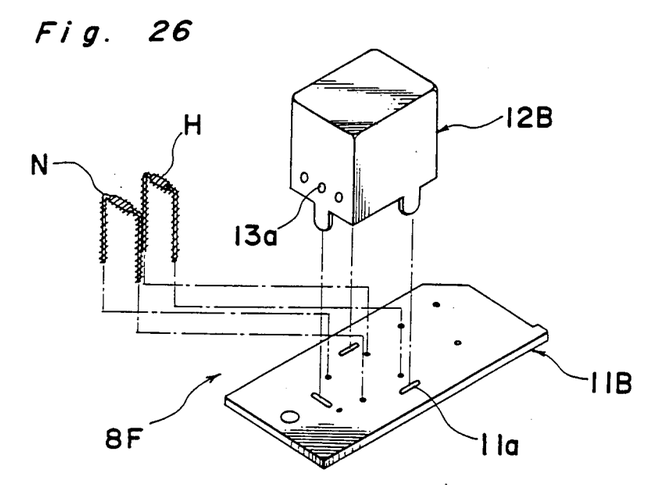
FIG. 26 is a view similar to FIG. 17, which particularly shows a seventh example of the humidity sensor.
Figure 27:
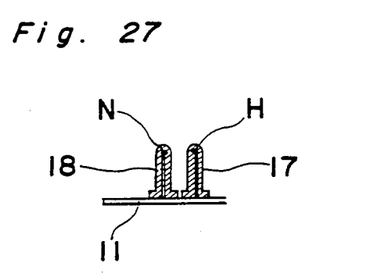
FIG. 27 is a sectional view of the temperature-detecting resistors of FIG. 26.

A seventh example of the humidity sensor 8F is illustrated in FIGS. 26 and 27, wherein synthetic resin films 17 and 18 are formed on the first and the second temperature-detecting resistors H and N, respectively. The synthetic resin films 17 and 18 are of a heat resistant material such as silicon resin, polyimide or the like, and entirely cover both of the leg portions 9A and 10A and the temperature detecting portions 9 and 10 of the temperature-detecting resistors H and N. The other construction of the humidity sensor 8F in this example is similar to that in the aforegoing third example.

By such construction as described hereinabove, the first and the second temperature-detecting resistors H and N are raised in thermal capacity, the variation in hm caused by the uneven air is reduced to eliminate the influence therefrom, and the output voltage is prevented from oscillation for the purpose of stabilization, and humidity detection which is high in accuracy can be performed.

Figure 28:
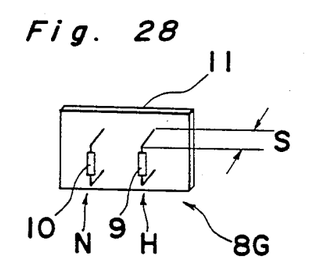
FIG. 28 is a view similar to FIG. 10, which particularly shows a eighth example of the humidity sensor.
Figure 29:
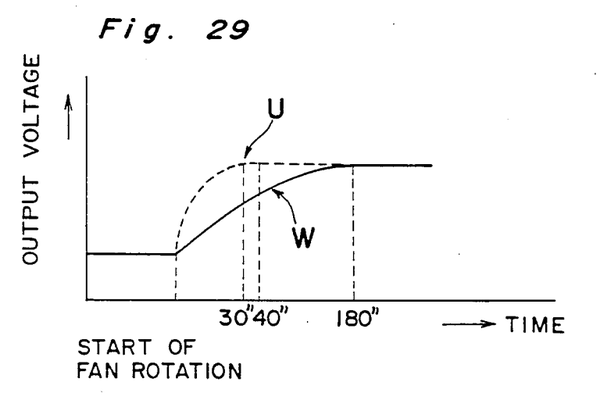
FIG. 29 is a graphical diagram showing an influence upon the output voltages from the humidity detecting circuit of FIG. 5 by a time constant of the temperature-detecting resistor with respect to heat.

FIGS. 28 and 29 show an eighth example of the humidity sensor 8G, wherein the temperature-detecting portions 9 and 10 of the first and the second temperature-detecting resistors H and N are spaced by 5 mm or more (S) from the base plate 11. It is to be noted that the other elements of the humidity sensor 8G in this example are similar to that in the above described second example.

As the cooling fan 3 does not rotate in a condition where the microwave oven is out of operation, with the temperature-detecting resistors H and N being mounted on the base plate 11 in close contact relation therewith as shown in FIGS. 9 and 10, the exhaust air never flows against the temperature-detecting resistors H and N and the base plate 11 so that the base plate 11 is heated by the self-heating temperature-detecting resistor H. Thereafter, upon rotation of the cooling fan 3 in a cooking mode, the exhaust air from inside the microwave oven flows against the temperature-detecting resistors H and N and the base plate 11. Since each of the temperature-detecting resistors H and N has a small time constant with respect to heat, they are brought into a thermal equilibrium condition after approximately thirty seconds from the start of rotation of the cooling fan 3.

However, since the base plate 11 is large in thermal capacity, it has a time constant of approximately three minutes with respect to heat. Accordingly, in the case where the temperature-detecting resistors H and N are mounted on the base plate 11 in close contact relation therewith, the circuit output is not stabilized until approximately three minutes have elapsed after the start of rotation of the cooling fan 3, as shown by a solid line W in FIG. 29.

On the contrary, when the temperature detecting portions 9 and 10 of the temperature-detecting resistors H and N are kept spaced by 5 mm or more from the base plate 11 as in this example, the heating of the base plate 11 by the self-heating temperature detecting resistor H is reduced. Furthermore, since heat insulating layers of the air are formed between the base plate 11 and the temperature-detecting resistors H and N with the rotation of the cooling fan 3, the heat stored on the base plate 11 exerts only an extremely small influence upon the temperature-detecting resistors H and N, thus resulting in the circuit output being stabilized in approximately thirty seconds as shown by a broken line U in FIG. 29, and being substantially dependent on the time constant of the temperature-detecting resistors H and N with respect to heat.

As apparent from the above description, the humidity detecting device for detecting humidity in the atmosphere within the ventilation passage is characterized in that the humidity sensor incorporated therein includes a first temperature-detecting resistor to be heated for detecting the ambient humidity, a second temperature-detecting resistor for detecting the ambient temperature and juxtaposed with the first temperature-detecting resistor, a base plate for supporting thereon the first and second temperature-detecting resistors and a rectifier box having a front plate and a rear plate facing the front plate for surrounding the first and second temperature-detecting resistors, with at least one inlet opening being defined in the front plate for controlling an air flow introduced into the rectifier box and at least one outlet opening being defined in the rear plate for controlling the air flow, said front and rear plates being provided so as to cross at a right angle to a direction of the air flow within the ventilation passage.

By the above described simple construction of the humidity sensor according to the present invention in which a rectifier box having an inlet and outlet opening for enabling air to pass therethrough is only provided so as to surround the temperature-detecting resistors in the humidity detecting device, uneven temperatures of the temperature-detecting portions caused under the influence of uneven air flow can be eliminated and correct humidity detection can be performed.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. A humidity detecting circuit for detecting ambient humidity in a surrounding environment, comprising:
   a constant current source;
   a first temperature-detecting resistor self-heated by said constant current source to detect ambient humidity;
   means for connecting one terminal of said first temperature-detecting resistor to an output terminal of said constant current source;
   a second temperature-detecting resistor for detecting ambient temperature;
   an operational amplifier having an inverting input terminal, an non-inverting input terminal and an output terminal;
   means for connecting said second temperature-detecting resistor between said one terminal of said first temperature-detecting resistor and said inverting input terminal of said operational amplifier so that the terminal voltage of said first temperature-detecting resistor is inputted to said inverting input terminal through said second temperature-detecting resistor;
   a feedback resistor associated with said operational amplifier; and
   means for connecting said feedback resistor between said inverting input terminal and said output terminal of said operational amplifier,
   an output voltage of said operational amplifier changing from a constant value upon the occurrence of humidity in said environment.

2. A humidity detecting circuit as claimed in claim 1, further comprising a resistance element and means for connecting said resistance element between said second temperature-detecting resistor and said inverting input terminal of said operational amplifier so that the terminal voltage of said first temperature-detecting resistor may be inputted into said inverting input terminal through said second temperature-detecting resistor and said resistance element.

3. A humidity detecting circuit as defined in claim 1, wherein said circuit is used in a microwave oven.

4. A humidity sensor incorporated in a humidity detecting device for detecting humidity within a ventilation passage, comprising:
   a first temperature-detecting resistor to be heated for detecting the ambient humidity;
   a second temperature-detecting resistor for detecting the ambient temperature and juxtaposed with said first temperature-detecting resistor;
   a base plate for supporting thereon said first and second temperature-detecting resistors; and
   a rectifier box having a front plate and a rear plate facing said front plate for surrounding said first and second temperature-detecting resistors, with at least one inlet opening defined in said front plate for controlling an air flow introduced into said rectifier box and at least one outlet opening defined in said rear plate for controlling said air flow, said front and rear plates being provided so as to cross at a right angle to a direction of said air flow within said ventilation passage.

5. A humidity sensor as claimed in claim 4, wherein said ventilation passage is part of a microwave oven.

6. A humidity detecting circuit for detecting ambient humidity in a surrounding environment, comprising:
   a constant current source;
   a first temperature-detecting resistor heated by said current source for detecting ambient humidity;
   a second temperature-detecting resistor for detecting ambient temperature;
   an operational amplifier having an inverting input terminal, a non-inverting input terminal, and an output terminal;
   a resistance element connected between one end of said second temperature-detecting resistor and said inverting input terminal;
   the other end of said second temperature-detecting resistor being connected to a terminal of said first temperature-detecting resistor for applying a terminal voltage of said first resistor to the inverting input terminal of the operational amplifier; and
   a feedback resistor connected between said inverting and output terminals of said operational amplifier;
   an output voltage of said operational amplifier changing from a constant value upon the occurrence of humidity in said environment.

7. A humidity detecting circuit as defined in claim 6, wherein said circuit is used in a microwave oven.

* * * * *